US008425485B2

(12) United States Patent
Tsuji et al.

(10) Patent No.: US 8,425,485 B2
(45) Date of Patent: Apr. 23, 2013

(54) ABSORBENT ARTICLE AND COMPOSITE SHEET

(75) Inventors: Tomoko Tsuji, Kagawa (JP); Hirotomo Mukai, Kagawa (JP); Kenichi Sasayama, Kagawa (JP); Tatsuya Hashimoto, Kagawa (JP); Kei Wakasugi, Kanonji (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 0 days.

(21) Appl. No.: 13/246,529

(22) Filed: Sep. 27, 2011

(65) Prior Publication Data

US 2012/0022486 A1 Jan. 26, 2012

Related U.S. Application Data

(63) Continuation of application No. 11/945,655, filed on Nov. 27, 2007, now Pat. No. 8,105,305.

(30) Foreign Application Priority Data

Nov. 27, 2006 (JP) ................................. 2006-319396

(51) Int. Cl.
*A61F 13/15* (2006.01)
(52) U.S. Cl.
USPC ............... 604/385.22; 604/385.24; 604/385.3
(58) Field of Classification Search ............. 604/385.22, 604/385.26, 385.29, 385.3
See application file for complete search history.

(56) References Cited

U.S. PATENT DOCUMENTS

| 4,655,760 A | 4/1987 | Morman et al. |
| 4,710,189 A | 12/1987 | Lash |
| 5,389,095 A | 2/1995 | Suzuki et al. |
| 5,451,219 A | 9/1995 | Suzuki et al. |
| 5,690,627 A | 11/1997 | Clear et al. |
| 5,876,391 A * | 3/1999 | Roe et al. ................... 604/385.3 |
| 5,882,769 A | 3/1999 | McCormack et al. |
| 6,362,391 B1 * | 3/2002 | Mizutani et al. .............. 604/379 |
| 8,105,305 B2 * | 1/2012 | Tsuji et al. ............... 604/385.26 |

FOREIGN PATENT DOCUMENTS

| EP | 0591647 | 4/1994 |
| GB | 2 271 315 | 4/1994 |
| GB | 2 297 474 | 8/1996 |
| JP | 5-228177 | 9/1993 |
| JP | 6-90979 | 4/1994 |
| JP | 10-245757 | 9/1998 |

(Continued)

OTHER PUBLICATIONS

Tsuji et al., U.S. Office Action mailed Apr. 28, 2010, directed to U.S. Appl. No. 11/945,655; 7 pages.

(Continued)

*Primary Examiner* — Lynne Anderson
(74) *Attorney, Agent, or Firm* — Morrison & Foerster LLP

(57) ABSTRACT

The present invention provides an absorbent article having a composite sheet with a plurality of gathers on an inner surface facing a wearer's body, which fits and adheres comfortably to the wearer's skin. The composite sheet is provided which includes a stretchable non-woven fabric which expands and contracts in at least one direction, a non-stretchable non-woven fabric, a junction which binds intermittently the stretchable non-woven fabric to the non-stretchable non-woven fabric in the stretching direction, and a plurality of gathers which is formed by loosening a unbounded area of the non-stretchable non-woven fabric in a contracted state, and is arranged along a direction intersecting the stretching direction, in which an apex of each gather does not reach the neighboring gather when the gathers lean to one side of the stretchable direction.

15 Claims, 8 Drawing Sheets

FOREIGN PATENT DOCUMENTS

| | | |
|---|---|---|
| JP | 2005-52225 | 3/2005 |
| JP | 2007-300940 | 11/2007 |
| WO | WO-94/14607 | 7/1994 |

OTHER PUBLICATIONS

Tsuji et al., U.S. Office Action mailed Nov. 10, 2010, directed to U.S. Appl. No. 11/945,655; 7 pages.

Tsuji et al., U.S. Office Action mailed Jun. 9, 2011, directed to U.S. Appl. No. 11/945,655; 7 pages.

Office Action mailed Feb. 13, 2012, directed to EG Application No. 2009050766; 5 pages.

Search Report dated May 31, 2012, directed to European Application No. 07832508.1; 6 pages.

* cited by examiner

ABSORBENT ARTICLE AND COMPOSITE SHEET

This application is a continuation of U.S. Ser. No. 11/945,655, filed Nov. 27, 2007, which claims the priority of Japanese Application No. 2006-319396, filed Nov. 27, 2006, the contents of all of which are incorporated herein by reference.

BACKGROUND OF THE INVENTION

1. Field of the Invention

The present invention relates to an absorbent article with a plurality of gathers on an inner surface facing the wearer's body when wearing and a composite sheet with a plurality of gathers.

2. Related Art

Conventionally, absorbent articles including, for example, disposable diapers, have been proposed. Disposable diapers are widely used for infants, children, elderly persons and physically handicapped persons, and have replaced reusable cloth absorbent article. Typical disposable diapers are generally composed of a composite structure including a top sheet, a back sheet and an absorbent body between the top and back sheets. The disposable diapers also include a stretchable composite sheet which gives stretchability to a non-stretchable sheet member for improved adhesion to a wearer's body and cushioning property. Such a stretchable composite sheet is realized, for example, by affixing two kinds of non-stretchable sheet members with an expanded stretchable member therebetween, which can be filiform, plexiform, strip-shaped, sheet-shaped and the like.

When the stretchable member of the stretchable composite sheet contracts, sheet members form large folds and can impart cushioning properties therefrom. However, when a wearer moves with a disposable diaper on, adhesion to a wearer's skin worsens and flexibility and texture deteriorates.

For the reasons stated above, for example, Japanese Unexamined Patent Application, Publication No. H05-228177 (hereinafter referred to as Patent Document 1) provides a shorts-type sanitary product using an elastic composite, obtained by attaching a non-woven base fabric to one or both sides of a contracted sheet-shaped elastic body to form gathers in a non-binding site between binding sites, which is joined to a non-woven base fabric side of a portion of the shorts to be stretchable.

The invention disclosed in Patent Document 1 has a structure referred to as floating gathers, which is realized by joining an elastic composite, obtained by binding an elastic body with a non-woven base fabric, to a portion to be stretchable of a shorts-type sanitary product. In the case of the shorts-type sanitary product disclosed in Patent Document 1, if the height of gathers is raised for improved elastic properties, the gathers are flattened and neighboring gathers overlap each other during wearing. This can deteriorate touch and comfort, and obstruct the expansion and contraction. Moreover, this can deteriorate adhesion to a wearer's body and result in a worsened ability to follow to a wearer's body while wearing.

SUMMARY OF THE INVENTION

The present invention was made in view of the aforementioned situation, and the objective is to provide an absorbent article with a plurality of gathers on an inner surface facing a wearer's body, which fits and adheres comfortably to the wearer's skin, and a composite sheet with a plurality of gathers which can give cushioning property when used.

In order to solve the above problems, the present inventors have conducted extensive examination. Consequently, the inventor has found that arranging a composite sheet, obtained by joining a stretchable non-woven fabric, which can expand and contract in at least one direction, to a non-stretchable non-woven fabric on an inner surface facing the wearer's body when wearing, gives a superior fit to the wearer's skin, thereby completing the present invention. More specifically, the present invention provides the following.

According to a first aspect of the present invention, an absorbent article is provided which includes an absorbent body and a chassis having at least a front body and a back body, in which the composite sheet constitutes or is arranged on the chassis; the composite sheet has a-stretchable non-woven fabric which expands and contracts at least in one direction, a non-stretchable non-woven fabric, a junction which binds intermittently the stretchable non-woven fabric to the non-stretchable non-woven fabric in the stretching direction, and a plurality of gathers in a non-bound portion between the junctions, formed of loosened parts of the non-stretchable non-woven fabric while the stretchable non-woven fabric is in a contracted state along a direction intersecting the stretching direction, and the gathers are arranged on a skin contacting side during wearing.

In a second aspect of the absorbent article as described in the first aspect of the present invention, the stretching direction includes a waist expanding direction of the absorbent article, and each of the gathers is arranged along the direction substantially orthogonal to the waist expanding direction.

In a third aspect of the absorbent article as described in the first or second aspect of the present invention, each of the gathers is arranged in an area including a position facing the buttocks of wearer when worn.

In a fourth aspect of the absorbent article as described in any one of the first to third aspects of the present invention, the composite sheet is arranged at a predetermined distance away, in the width direction, from a centerline equally dividing the back body, and at each of a pair of areas that are symmetrical to the centerline.

In a fifth aspect of the absorbent article as described in any one of the first to fourth aspects of the present invention, a first gather and a second gather, which is adjacent thereto in the stretching direction of the gathers, are formed not to overlap each other in a case where the first and the second gathers lean.

In a sixth aspect of the absorbent article as described in the fifth aspect of the present invention, the absorbent article satisfies the following Formula 1 in which A is a width in the stretching direction of a junction where the non-stretching non-woven fabric is bound to the stretching non-woven fabric, B is a length in the stretching direction of the region of the non-stretchable non-woven fabric not bound to the stretchable non-woven fabric, and C is a distance in the stretching direction between each of the junctions.

$$B < C + 2A \qquad \text{Formula 1}$$

In a seventh aspect of the absorbent article as described in any one of the first to sixth aspects of the present invention, a first gather and a second gather, which is adjacent thereto in the stretching direction of the gathers, are formed not to overlap each other in a case the first and the second gathers lean facing each other.

In an eighth aspect of the absorbent article as described in the seventh aspect of the present invention, the absorbent article satisfies the following Formula 2 in which A is a width in the stretching direction of a junction where the non-stretching non-woven fabric is bound to the stretching non-woven fabric, B is a length in the stretching direction of the region of the non-stretchable non-woven fabric not bound to the stretchable non-woven fabric, and C is a distance in the stretching direction between each of the junctions.

$$B < A + C \qquad \text{Formula 2}$$

According to a ninth aspect of the present invention, a composite sheet is provided which includes: a stretchable non-woven fabric which expands and contracts in at least one direction; a non-stretchable non-woven fabric; a junction which binds intermittently the stretchable non-woven fabric to the non-stretchable non-woven fabric in the stretching direction; and a plurality of gathers which is formed by loosening a unbounded area of the non-stretchable non-woven fabric in a contracted state, and is arranged along a direction intersecting the stretching direction, in which an apex of each gather does not reach the neighboring gather when the gathers lean to one side of the stretchable direction.

The present invention can provide an absorbent article and a composite sheet that fit and adhere comfortably to a wearer's skin.

DETAILED DESCRIPTION OF THE INVENTION

Preferred embodiments of the present invention are described in detail below. It should be noted that the present invention is not limited thereto, and can be changed and implemented as necessary to implement in the scope of the objective of the present invention. It should also be noted that, although redundant descriptions are omitted, the present invention is not limited thereby.

In the preferred embodiments, it is assumed that the side of the disposable diaper facing a wearer's body is a skin contacting side, and the side opposite the skin contacting side is a skin non-contacting side.

First Embodiment of an Absorbent Article

Figure 1:
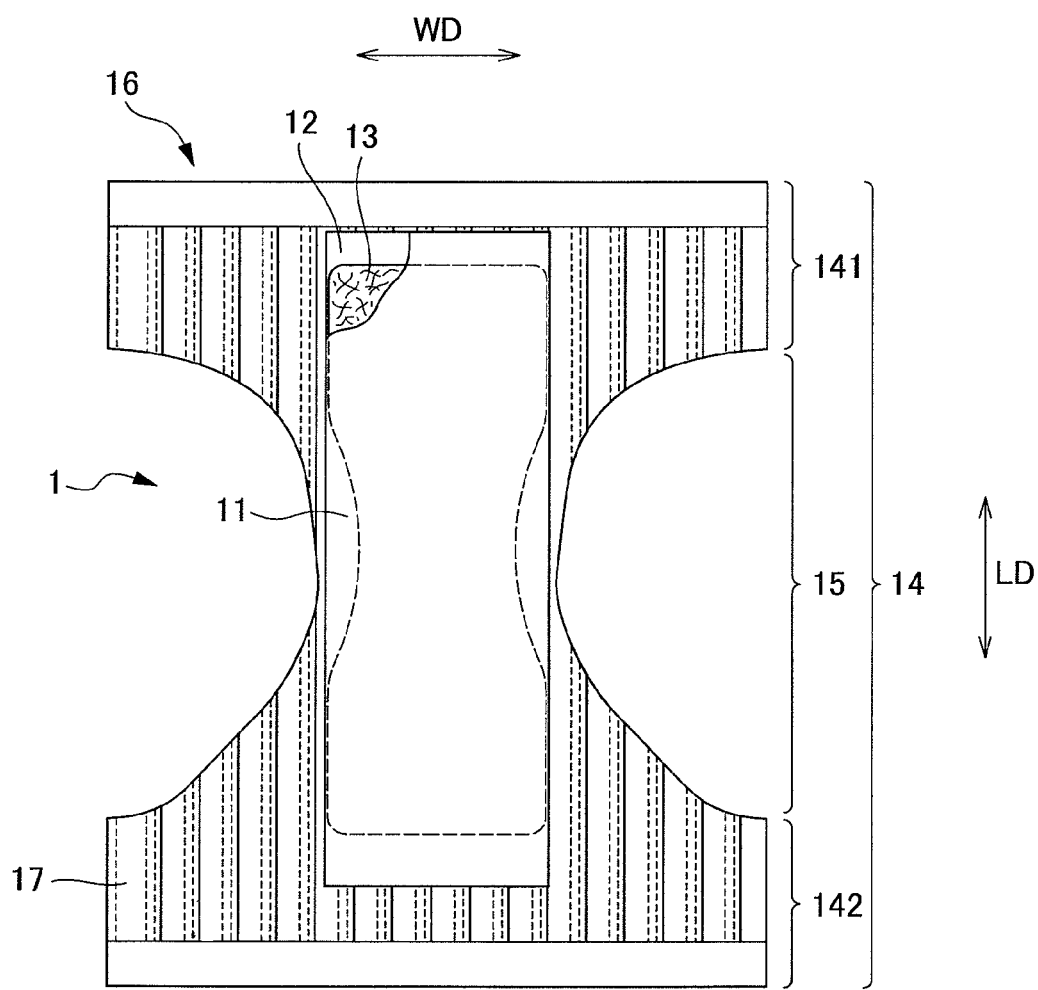
FIG. 1 is a top view of a main body of the disposable diaper in a flattened state.
Figure 2:
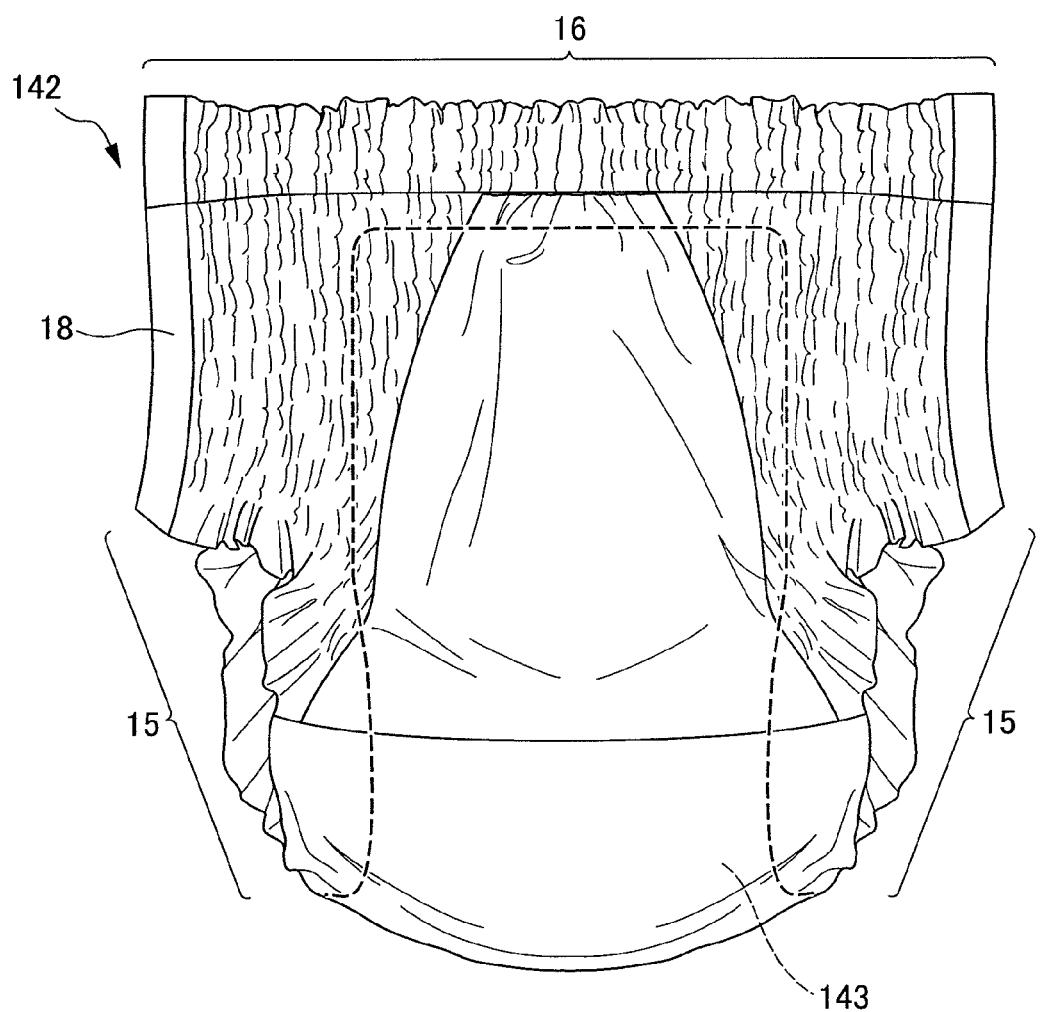
FIG. 2 is a front view of a main body of the disposable diaper.

FIG. 1 is a top view of a disposable diaper in the flattened state according to a first embodiment of the present invention. FIG. 2 is a front view of a main body of the disposable diaper. The disposable diaper 1 includes a chassis 14, a liquid permeable top sheet 11, a liquid impermeable back sheet 12 and a liquid retentive absorbent body 13. The chassis 14 forms the outline of the disposable diaper 1, and is composed of a front body 141 and a back body 142 that are shaped into a shorts shape during wearing. The liquid permeable top sheet 11 is disposed on the skin-contacting side of the chassis 14, and has a substantially elongated shape forming a top layer. The liquid impermeable back sheet 12 is disposed on the skin non-contacting side of the chassis 14 as one side of the top sheet 11, and has a substantially elongated shape forming a back layer. The liquid retentive absorbent body 13 is disposed between the top sheet 11 and the chassis 14, and has a substantially elongated shape forming an absorbent layer. It should be noted that the term substantially elongated shape includes a shape in which a portion of both sides in the longitudinal direction LD is tapered to the center in the longitudinal direction LD or bulged in the direction opposite the center. Specifically, the absorbent body 13 includes an absorbent body 13 that is different in length in the width direction WD in a portion in the longitudinal direction LD.

The absorbent body 13 may be arranged in the state of being covered with tissues (not shown) or a hydrophilic non-woven fabric (not shown). When covered with a hydrophilic non-woven fabric, the absorbent body 13 may be configured without application of the liquid permeable top sheet 11 or with only a partial application thereof. This allows for a reduction in manufacturing cost, for example.

The chassis 14 includes a front body 141, a back body 142, and a crotch 143 arranged therebetween during wearing. The chassis 14 is formed to provide a shorts shape by joining the front body 141 and the back body 142 at predetermined locations of the front body 141 and the back body 142. Specifically, the chassis 14 includes a waist opening 16 formed around a wearer's abdomen and a pair of leg openings 15 formed around a wearer's legs during wearing. It should be noted that the predetermined location of the front body 141 and the back body 142 designates both ends of the front body 141 and the back body 142 in the direction (referred hereafter to as width direction WD) orthogonal to the rise direction RD in the worn state except for the leg openings 15. The front and rear bodies 141 and 142 include, for example, front and rear bodies distinguished by the center line parallel to the width direction WD, which bisects the disposable diaper 1 in the longitudinal direction LD.

The front and rear bodies 141 and 142 are composed of, or arranged by, a composite sheet 17 obtained by laminating (joining) a stretchable non-woven fabric 172 and a non-stretching non-woven fabric 171. The composite sheet 17 is arranged between a waist opening 16 and a pair of leg openings 15. In the present embodiment, the composite sheet 17 expands and contracts in the width direction WD. A plurality of gathers (or folds) 174 is formed of a non-stretchable non-woven fabric 171 on one side (skin contacting side in the present embodiment) of a stretchable non-woven fabric 172 of a composite sheet 17. The plurality of gathers 174 is arranged along a direction intersecting the stretching direction of the composite sheet 17. For example, each of the plurality of gathers 174 is arranged along a direction (longitudinal direction LD) substantially orthogonal to the width direction WD. Each of the plurality of gathers 174 is formed in the width direction WD at substantially equal intervals.

The disposable diaper body 1 is formed to provide a shorts shape, including a trunk opening 16 and a pair of leg openings 15, by joining the front body 141 and the back body 142 at the junctions 18 as shown in FIGS. 1 and 2.

It should be noted that, although a disposable diaper body 1 is described in the preferred embodiments, the present invention is not limited thereto. For example, it may be a disposable diaper body 1 formed to provide a shorts shape, including a trunk opening 16 and a pair of leg openings 15, by joining the front body 141 and the back body 142 at the junctions 18. It may also be used in an expansion-type disposable diaper which can be worn by engaging the front body 141 and the back body 142 with an engaging member and the like.

Alternatively, an engaging member such as a surface fastener used in the expansion-type disposable diaper 1 may be disposed at the junction 18 in the front body 141 and the rear body 142 of a pants-type disposable diaper. This provides a disposable diaper of a pants-type that can be expanded and re-engaged by easy release and engagement.

Furthermore, in the present invention, a leak preventing wall (not shown), which can be formed by using a leak preventing sheet, may be arranged along both ends in the width direction (WD) of the absorbent body 13 of the disposable diaper.

Although a liquid impermeable back sheet 12 is arranged on the skin non-contacting side, without being limited thereto, the back sheet 12 may be arranged between the absorbent body 13 and the chassis 14 or between sheets when the chassis 14 includes a plurality of sheets.

In this case, the liquid permeable top sheet 11 and the absorbent body 13 are adhesively joined to each other with a hot-melt adhesive. In addition, the liquid permeable top sheet 11 and absorbent body 13 are adhesively joined to the chassis 14 with the hot-melt adhesive. In a similar way, the chassis 14 and the liquid impermeable back sheet 12 are adhesively joined to each other with the hot-melt adhesive.

The front body 141 and back body 142 are intermittently joined at the junction 18 using ultrasonic sealing. As another connecting method at the junction 18, hot sealing or a hot-melt adhesive may be used to make the connection.

For the disposable-diaper main body, a plurality of filiform elastic members (not shown) are arranged at the circumference of the waist opening 16. The elastic members may be strip-shaped. The elastic members may include an elastic sheet that can stretch, such as a stretchable non-woven fabric (non-woven fabric formed of mixed fibers of polyurethane and polypropylene or the like), a stretchable film or the like.

In the disposable diaper body 1, the inner surface facing the wearer's skin is composed of the composite sheet 17 including the non-stretchable non-woven fabric 171 and the stretchable non-woven fabric 172.

Figure 5:
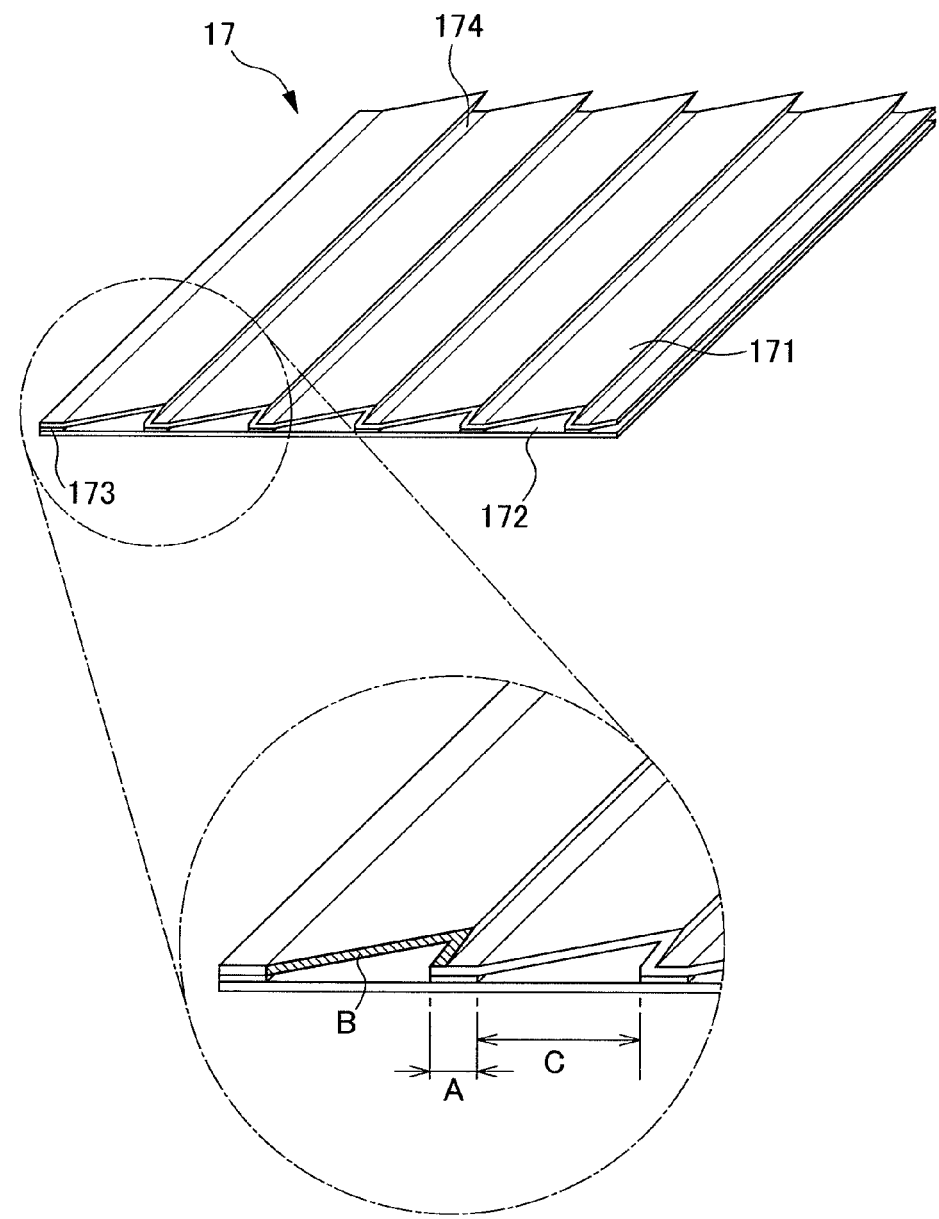
FIG. 5 is a perspective view of the composite sheet.
Figure 6:
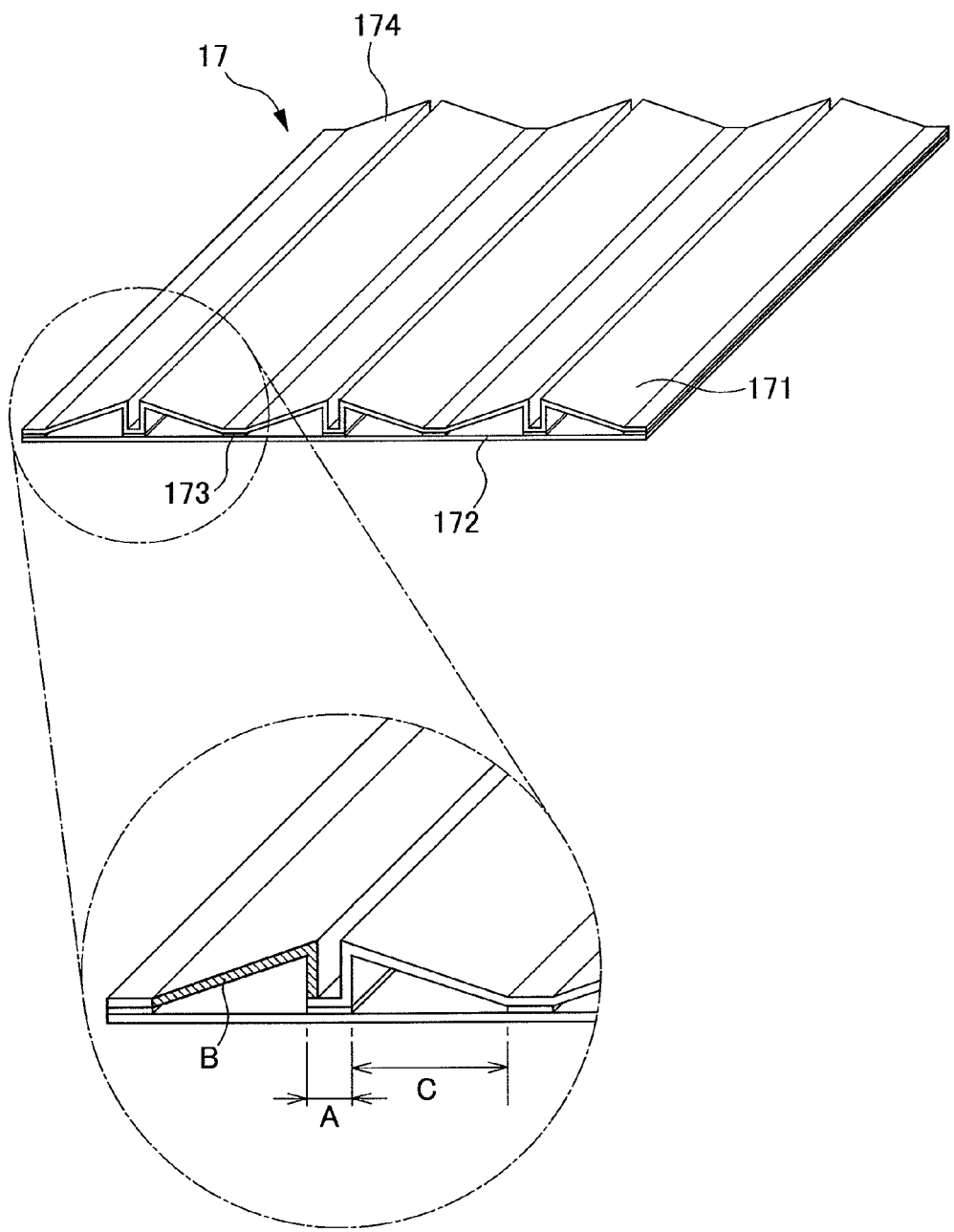
FIG. 6 is a perspective view of the composite sheet.

Next, the composite sheet 17 according to the present invention is described. FIGS. 5 and 6 are perspective views of the composite sheet 17. The composite sheet 17 is a sheet obtained by joining the expanded stretchable non-woven fabric 172 with the non-stretchable non-woven fabric 171 at regular intervals, which includes a plurality of gathers 174 which is continuously formed in the direction orthogonal to the contracting direction of the stretchable non-woven fabric 172 in a non-expanded state. Non-stretchable non-woven fabric 171 is bound to the stretchable non-woven fabric 172 at the junction 173. The junction 173 is formed in a stretching direction at regular intervals. A non-joined part (B in FIGS. 4 and 5), in which the non-stretchable non-woven fabric 171 is not bound to the stretchable non-woven fabric 172, constitutes the plurality of gathers 174 successive in the direction orthogonal to the stretching direction of the stretchable non-woven fabric 172. The gathers 174 are formed by a slack portion in the stretch direction of the non-stretchable non-woven fabric 171. Meanwhile, the gathers 174 are formed not to overlap each other even when the stretchable non-woven fabric 172 is not expanded.

The plurality of gathers 174 can be formed to be tilted to the same direction in the stretching direction as shown in FIG. 5, formed to be tilted facing each other in the stretching direction as shown in FIG. 6, or formed to be tilted randomly in the stretching direction of the stretchable non-woven fabric 172, in other words, a mixed configuration of FIGS. 5 and 6. It should be noted that although the gathers 174 shown in FIGS. 5 and 6 have sharp folding lines, the folding lines actually are not sharp and are constructed with material of superior feel.

Material for the non-stretchable non-woven fabric 171 can be appropriately selected from, for example, various conventionally-known non-stretchable non-woven fabrics, such as spunbonded non-woven fabric, SMS non-woven fabric, point-bonded non-woven fabric, through-air non-woven fabric, spunlace non-woven fabric, and needlepunched non-woven fabric, in accordance with the intended purposes of the absorbent article. These fabrics may be used alone or in combination. Fiber for the non-stretchable non-woven fabric 171 can be a sheath-core type composite fiber made of polypropylene, polyolefin, polyester, polyamide, polyethylene/polypropylene or polyethylene/polyester, or a side-by-side composite fiber.

The weight of the non-stretchable non-woven fabric 171 can be appropriately selected in accordance with the intended purpose; however, the preferred weight is from 10 to 50 g/m$^2$. When the weight is lower than 10 g/m$^2$, the strength of the non-stretchable non-woven fabric 171 can deteriorate. On the other hand, when the weight exceeds 50 g/m$^2$, stiffness can be increased and stretchability can be impaired.

The stretchable non-woven fabric 172 can be produced by a conventionally known drawing method such as a gear processing method, and the composite sheet 17 may be constructed with gear-processed stretchable non-woven fabric 172 and the non-stretchable non-woven fabric 171. In manufacturing the composite sheet 17, to make the sheet stretchable, a margin can be made on the non-stretchable non-woven fabric 171, and then the stretched stretchable non-woven fabric 172 can be joined thereto.

Material for the gear-processed stretchable non-woven fabric 172 can be appropriately selected from, for example, various conventionally-known non-woven fabrics such as spunbond non-woven fabric, melt-blown non-woven fabric, heat rolled non-woven fabric, SMS non-woven fabric consisting of spunbond and melt-blown non-woven fabrics, through-air non-woven fabric, spunlace non-woven fabric and air-laid non-woven fabric in accordance with the intended purposes of the absorbent article. These fabrics may be used alone or in combination. Resins constituting these stretchable non-woven fabrics 172 may be, for example, elastomer resins such as polystyrene, polyurethane and the like; thermoplastic resins such as polyethylene, polypropylene, polyester, acrylic and the like; and composite fiber such as polyethylene/polypropylene, polyethylene/polyethylene terephthalat-e and the like (such as core-in-sheath fiber and side-by-side fiber). These resins may be used alone or in combination.

Materials for the entire stretchable non-woven fabric being not gear-processed can be appropriately selected from, for example, various conventionally-known stretchable non-woven fabrics, such as spunbonded non-woven fabric, point-bonded non-woven fabric, through-air non-woven fabric, chemically bonded non-woven fabric, melt-blown non-woven fabric, spunlace non-woven fabric, and needlepunched non-woven fabric in accordance with the intended purposes of the absorbent article. Fiber for the stretchable non-woven fabric 172 can be elastomer resins such as polystyrene, polyurethane and the like; thermoplastic resin such as polyethylene, polypropylene, polyester, acrylic and the like; or sheath core type or side-by-side composite fiber made of polyolefin, polyester, polyamide, polyethylene/polypropylene or polyethylene/polyester. In addition, a stretchable non-woven fabric 172 can be used, obtained by melt-spinning a urethanebased thermoplastic synthetic resin to obtain a spunbond non-woven fabric, and drawing the spunbond non-woven fabric at least in one direction to generate elasticity.

The weight of the stretchable non-woven fabric 172 (non-expanded state) can be appropriately selected in accordance with the intended purposes; however, the preferred weight is from 10 to 80 g/m². When the weight is lower than 10 g/m², the strength of the stretchable non-woven fabric 172 can deteriorate. On the other hand, when the weight exceeds 80 g/m², the preferred stretching property cannot be obtained due to the increased stretching stress of the stretchable non-woven fabric 172 and the increased skew in a case of using a thermoplastic resin.

In addition, the strength of the stretchable non-woven fabric 172 (expanded to 200%) is preferably equal to or less than 10 N/50 mm, and more preferably in the range of 1 to 7 N/50 mm.

The strength of the stretchable non-woven fabric 172 in a 200% expanded state is measured by the following procedures. It is assumed that the stretching direction of the composite sheet 17 is the longitudinal direction, and the direction orthogonal to the stretching direction is the width direction. A test piece is obtained from the non-expanded composite sheet 17 of 50 mm in the width direction and 100 mm in the lengthwise direction. Using an autograph-type tensile test machine (AG-1kNI), with a grip spacing of 50 mm (inner size when an upper and a lower part of the test piece are held by chucks), and a measuring speed of 500 ram/min, strength at the next site (when the test piece is expanded to 200% (grip spacing of 100 mm)) is measured.

Even more particularly, after being expanded to 200%, skewness of the stretchable non-woven fabric 172 is preferably no more than 15%, and more preferably no more than 10%.

The weight of the composite sheet 17 in a non-expanded state is preferably in the range of 30 to 200 g/m², and more preferably in the range of 65 to 105 g/m². If the weight is less than 30 g/m², the composite sheet 17 may be torn due to lack of uniformity and partially deteriorated strength. On the other hand, if the weight of the composite sheet 17 exceeds 200 g/m², air permeability is obstructed and a high-temperature high-moisture state may result therefrom after wearing for a long time. The weight of the non-stretchable non-woven fabric 171 by itself is preferably in the range of 10 to 50 g/m².

The non-stretchable non-woven fabric 171 is bound to the stretchable non-woven fabric 172 at the junction 173 at regular intervals. If the gathers 174 of the non-stretchable non-woven fabric 171 is tilted to the same direction when the stretchable non-woven fabric 172 is not expanded (in the case of FIG. 5), the interval (C in FIGS. 5 and 6) and the height of a gather 174 preferably satisfy the following Formula 3 when the non-stretchable non-woven fabric 171 and the stretchable non-woven fabric 172 are bound to each other:

$$B < C + 2A \qquad \text{Formula 3}$$

(in which A is a width of the junction 173 in the stretching direction where the non-stretching non-woven fabric 171 is bound to the stretching non-woven fabric 172, B is a length in the stretching direction of the area of the non-stretchable non-woven fabric 171 not bound to the stretchable non-woven fabric 172, and C is a distance between the junctions 173 in the stretching direction).

By binding the non-stretchable non-woven fabric 171 and the stretchable non-woven fabric 172 so that Formula 3 is satisfied, a first gather and a second gather, which is adjacent thereto in the stretching direction, of the plurality of gathers 174 can be formed not to overlap each other in a case where the first and the second gathers lean to the same side in the stretching direction. In other words, in a case where the composite sheet 17 is not expanded, the non-stretchable non-woven fabric 171 is stabilized having gathers 174 (or slacks) in the area between itself and the neighboring junction 173. In the case in which the neighboring first and the second gathers of the gathers 174 (slacks) are forced to be flattened in the same direction, an apex of the first gather does not reach the second gather adjacent thereto. In other words, apexes of the gathers 174 (slacks) do not exceed the junction 173 even when flattened.

This results in a thin composite sheet 17 with low stiffness. Moreover, the composite sheet 17 provides superior comfort and adhesion to a wearer's body during wearing, since the gathers 174 do not create friction against each other. The composite sheet 17 can also prevent friction against the wearer's body.

If the gathers 174 are tilted facing each other (in the case of FIG. 6) when the stretchable non-woven fabric 172 is not expanded (in the case of FIG. 5), the non-stretchable non-woven fabric 171 and the stretchable non-woven fabric 172 are preferably bound to each other to satisfy the following $$B < A + C \qquad \text{Formula 4}$$

(in which A is a width of the junction 173 in the stretching direction where the non-stretching non-woven fabric 171 is bound to the stretching non-woven fabric 172, B is a length in the stretching direction of the area of the non-stretchable non-woven fabric 171 not bound to the stretchable non-woven fabric 172, and C is a distance between the junctions 173 in the stretching direction).

By binding the non-stretchable non-woven fabric 171 and the stretchable non-woven fabric 172 so that Formula 4 is satisfied, a predetermined gather 174 and another predetermined gather 174 adjacent thereto can be formed not to overlap each other. In other words, in a case where the composite sheet 17 is not expanded, the non-stretchable non-woven fabric 171 is stabilized having gathers 174 (or slacks) in the area between itself and the neighboring junction 173. In the case in which the neighboring first and the second gathers of the gathers 174 (slacks) are forced to be flat facing each other, the apex of the first gather does not reach the second gather adjacent thereto. In other words, apexes of the gathers 174 (slacks) do not exceed the junction 173 even when flattened.

This results in a thin composite sheet 17 with low stiffness. Moreover, the composite sheet 17 provides excellent comfort and adhesion to the wearer's body, since the gathers 174 do not create friction against each other.

It should be noted that an elastic member (not shown) can intervene in the absorbent article shown in FIGS. 1 to 4 as necessary. The shape of the elastic member is not particularly limited and can be appropriately selected in accordance with the intended purposes. For example, the elastic member can be strip-shaped, sheet-shaped, plexiform or filiform. The abovementioned elastic members can be used singly or in combination of two or more types to constitute a disposable diaper body 1.

According to the disposable diaper body 1 of the present embodiment, a first gather and a second gather adjacent thereto in the stretching direction of a plurality of gathers 174 are formed not to overlap each other, thus resulting in a thin absorbent article with low stiffness. Moreover, the gathers 174 do not create friction against each other. Therefore, a thin, soft absorbent article can be provided, which fits and adheres comfortably to the wearer's skin.

Additionally, a low apparent thickness and a low repulsive force of the sheet enable easy folding and compact packaging.

Second Embodiment of an Absorbent Article

Figure 3:
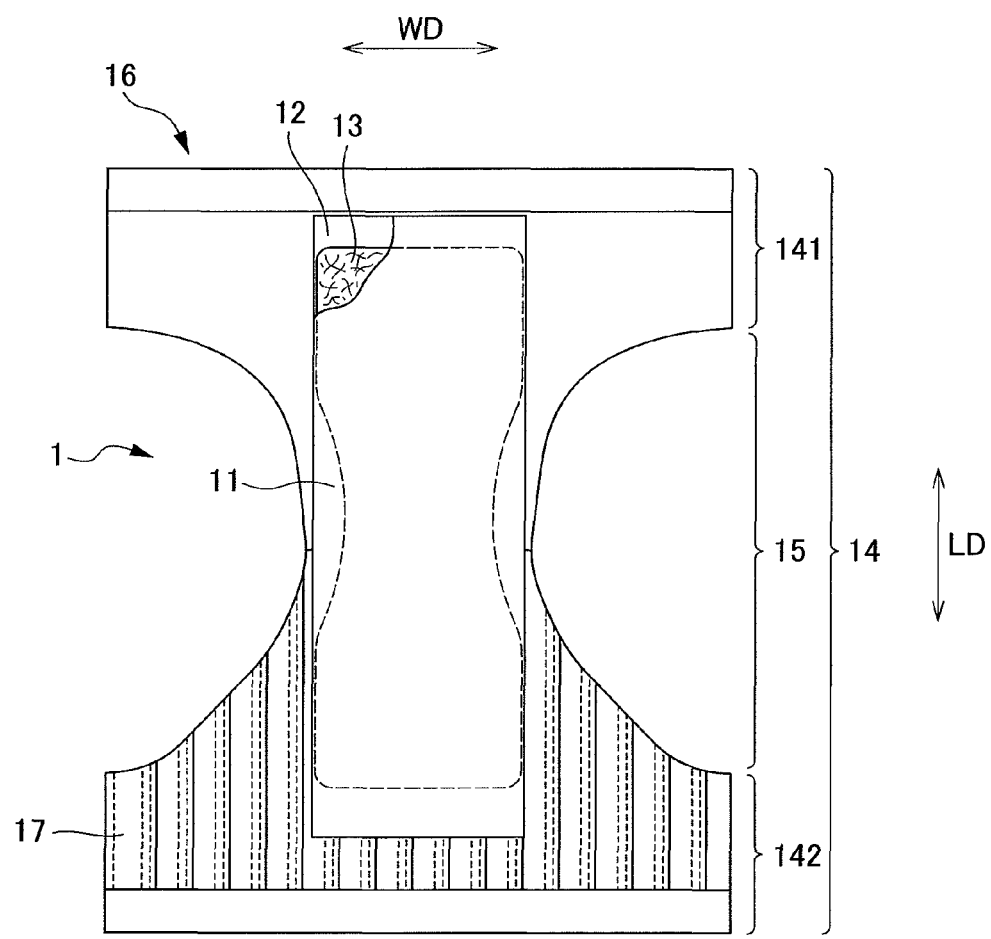
FIG. 3 is a top view of a main body of the disposable diaper with a composite sheet arranged in the back body in the flattened state.
Figure 4:
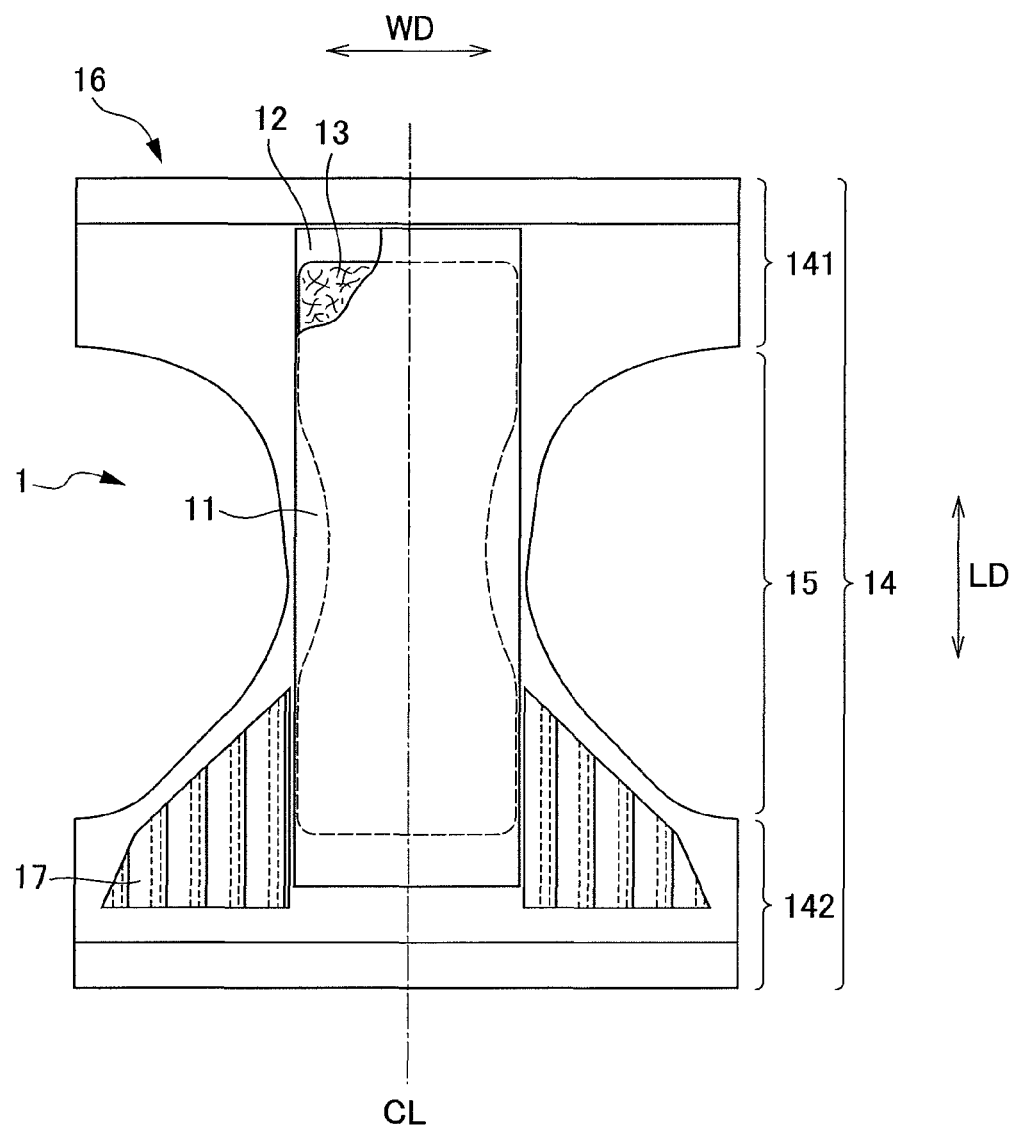
FIG. 4 is a top view of a main body of the disposable diaper with a composite sheet arranged in the vicinity of the buttocks in the flattened state.

FIGS. 3 and 4 are top views of a disposable diaper in a flattened state according to a second embodiment of the present invention. The second embodiment is similar to the first embodiment except that a plurality of gathers 174 of the composite sheet 17 is arranged selectively in and around the back body 142.

The present inventors have found through measuring lower-back movement of a wearer with a disposable diaper body 1 on during resting and during walking, using a DLT (Direct Linear Transformation) method that adhesion of the disposable diaper body 1 to the wearer's body is the worst at the vicinity of the buttocks. In other words, the inventors have found that if adhesion in the vicinity of the buttocks can be improved, the comfort of the whole disposable diaper body 1 can be improved. Thus, as shown in FIG. 3, the composite sheet 17 can be arranged in the vicinity of the back body 142 of the disposable diaper body 1, namely on the skin contacting side of the area contacting the wearer's buttocks (back body) during wearing.

Alternatively, having determined areas of the worst adhesion to the wearer's body by the DLT method, the composite sheet 17 can be arranged only in the specified areas in the area contacting the wearer's buttocks (as shown in FIG. 4). In this case, the composite sheet is arranged at a predetermined distance away, in the width direction WD, from a centerline CL equally dividing the back body, and at each of a pair of areas that are symmetrical to the centerline CL.

According to the disposable diaper body 1 of the present embodiment, in addition to the effect of the first embodiment, by arranging the composite sheet 17 at the areas of the worst adhesion to the wearer's body, in the area contacting the wearer's buttocks, an absorbent article of superior comfort can be provided. In addition, an absorbent article of superior ability to follow can also be provided.

Composite Sheet

The composite sheet 17 stated above can be used as a composite sheet for an inner covering of the absorbent article, in addition to the use for the disposable diaper body 1. Such a composite sheet is thin, superior in flexibility and in feel, has superior cushioning property, and thus can be used for sanitary products in addition to disposable diapers.

Manufacturing Method for Composite Sheet.

The composite sheet 17 is obtained, as stated above, by laminating (binding) a non-stretchable non-woven fabric 171 and a stretchable non-woven fabric 172. Firstly, a stretchable non-woven fabric 172 is produced by gear processing.

Figure 7:
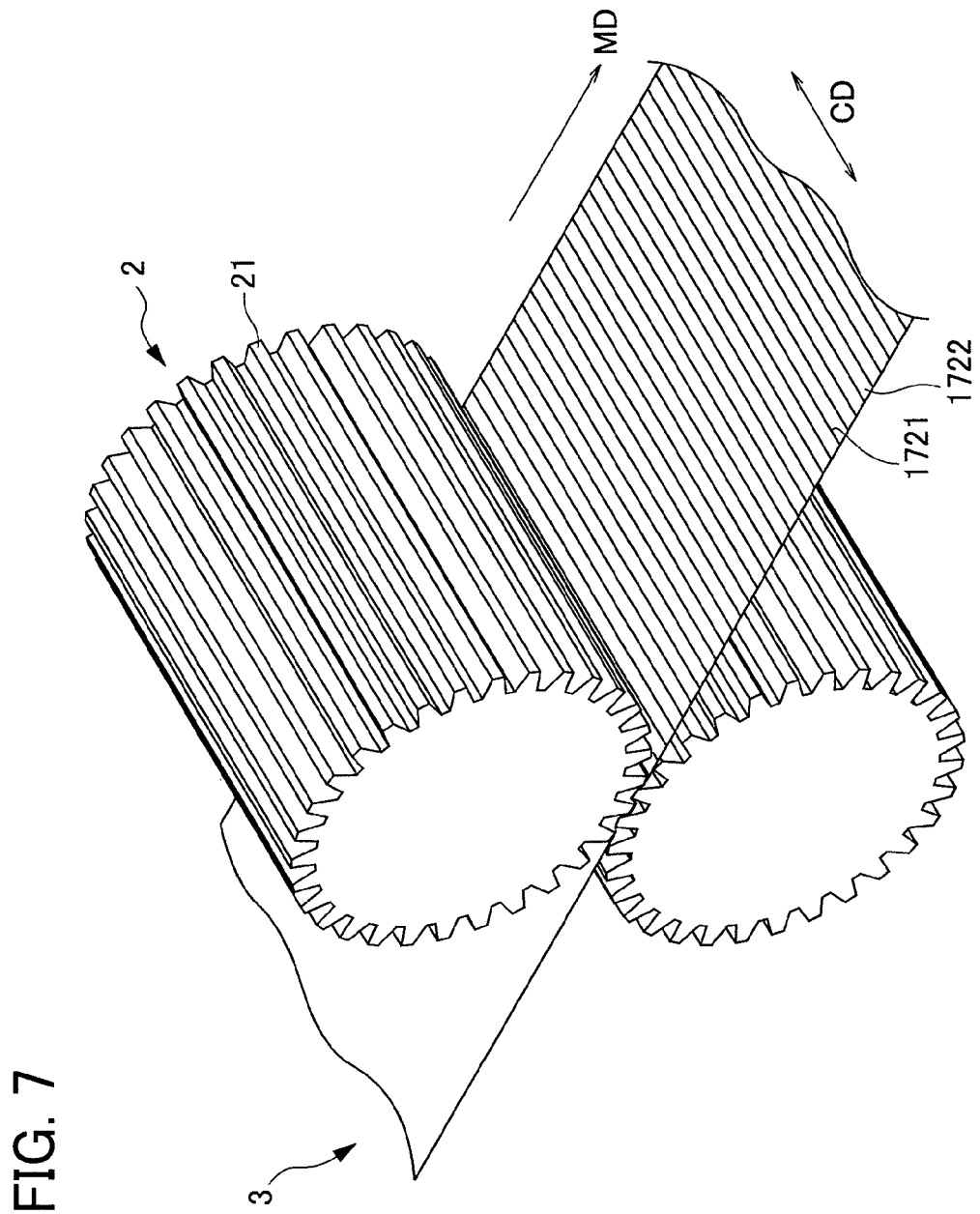
FIG. 7 is a diagram showing an example of manufacturing the stretchable non-woven fabric.

FIG. 7 is a diagram showing a method of manufacturing a stretchable non-woven fabric 172 by gear processing. A stretchable non-woven fabric is manufactured by compressing a high-density sheet 3 by a gear edger 2 such as a pair of embossing rolls shown in FIG. 7, thus stretching the sheet 3 to obtain low-density areas 1722. The gear edger 2 has a cog area 21 in which a plurality of cogs is arranged. A pair of the gear edgers 2 rotates facing each other with the sheet 3 therebetween and engages each other, thus compressing and reducing the thickness of the sheet 3 by the pressure at the apex of the cog area 21. By rotating a pair of gear edgers 2 tucking the sheet 3, the sheet 3 is compressed by the cog area 21, and high-density regions 1721 and low-density regions 1722 are obtained alternately at the interval of the cogs.

The method shown in FIG. 7 includes a mating plate, embossing, thermoforming, high-pressure hydraulic molding and injection molding. In addition to the manufacturing method shown in FIG. 7, in the case using a low-density non-woven fabric, for example, the non-woven fabric can be once melted and formed into a film by heat or ultrasonic processing to add high-density regions 1721. In this case, a heat-treated region becomes a high-density region 1721, and an untreated region becomes a low-density region 1722. Even more particularly, for example, the high-density regions 1721 may be formed by collective embossed lines or dots. In addition to a gear-processed stretchable non-woven fabric 172, a stretchable non-woven fabric 172 obtained by drawing a non-drawn non-woven sheet can be used.

In particular, for example, by drawing a non-woven fabric produced by a spunbond method in a machine direction MD, an appropriate stretchability in width and lengthwise directions can be obtained. Additionally, by combining a non-stretchable non-woven fabric 171, a strength required for an absorbent article can be obtained. In FIG. 7, MD is a direction parallel to a machine direction of a fiber web at the production of the stretchable non-woven fabric 172. CD is a direction orthogonal to the machine direction of the fiber web, namely MD.

A heating method, drawing temperature, and drawing ratio of the drawing processing of a non-drawn non-woven sheet can be appropriately set in accordance with the intended purposes of composite sheet 17.

The stretchable non-woven fabric 172 obtained by the drawing processing is expanded and bound to a non-stretchable non-woven fabric 171 via a junction 173 (for example, see FIG. 5). Even more particularly, the stretchable non-woven fabric 172 is bound to the non-stretchable non-woven fabric 171 being expanded preferably at least to 150%, and more preferably to approximately 200%. If the stretchable non-woven fabric 172 is bound in a state being expanded to less than 150%, a stretchability required for a composite sheet 17 may not be fully obtained.

The binding method is not particularly limited, but each non-woven fabric preferably adheres only at the junction 173 by hot-melt adhesion using an elastomer-based resin as a major component. Since the coating pattern of hot-melt adhesion is arranged intermittently in the stretching direction on a non-bound portion of the non-stretchable non-woven fabric 171 (B of FIG. 4 or 5) in a direction orthogonal to the stretching direction, successive gathers 174 are easily developed when the stretchable non-woven fabric 172 contracts. The coating patterns of hot-melt adhesion include pattern coating or solid pattern coating such as spiral coating, controlled seam coating, coater coating, curtain coater coating, summit-gun coating, curtain spray coating, omega coating, whole coating, multi-dot coating, etc., for example. The weight of an adhesive for hot-melt adhesion is preferably in the range of 1 to 5 g/m$^2$. It should be noted that it is obvious that the non-stretchable non-woven fabric 171 adheres only to the junction 173 so that the Formula 3 or 4 is satisfied. Once the non-stretchable non-woven fabric 171 and the stretchable non-woven fabric 172 are bound and the stretchable non-woven fabric 172 contracts, a plurality of gathers 174 is compressed by an edger or a belt to tilt to the same side as shown in FIG. 4, or to tilt facing each other as shown in FIG. 5.

EXAMPLES

Examples of the present invention are described hereafter. However, these examples are illustrative only and the present invention should not be construed as being limited to these examples.

Areas of the worst adhesion to a wearer's body were determined in a disposable diaper 1 by the DLT method. A disposable diaper body 1 was prepared with composite sheets 17 arranged in the areas of the worst adhesion, the vicinity of the buttocks, as shown in FIG. 4 (hereinafter referred to as Example 1). Then, subjective evaluation was undertaken by 12 female panel members in their late fifties to seventies to assess fit and adhesion to the wearer's skin and comfort during wearing thereof. The comfort during wearing was assessed by comfortable fit of the disposable diaper body 1 and pleasant texture of an absorbent body 13.

The subjective evaluation included steps of: wearing a marketed disposable diaper, assessing the comfort immediately after putting on, assessing the comfort with various postures such as sitting on a chair, sitting with legs folded under the body and squatting, and assessing the comfort after three minutes of walking. The marketed disposable diaper was used as a standard sample and hereinafter is referred to as Standard Example.

The subjective evaluation also included steps of: wearing Example 1 and assessing the comfort during wearing in the same way as with Standard Example. Assessment was made based on an eleven point scale from −5 (the worst) to +5 (the best), relative to a comfort of Standard Example as 0.

The subjective evaluation also included steps of: wearing two other marketed disposable diapers (hereinafter referred to as Comparative Examples 1 and 2) and assessing the comfort during wearing in the same way as with Example 1. The results are shown in FIGS. 8 and 9.

Figure 8:
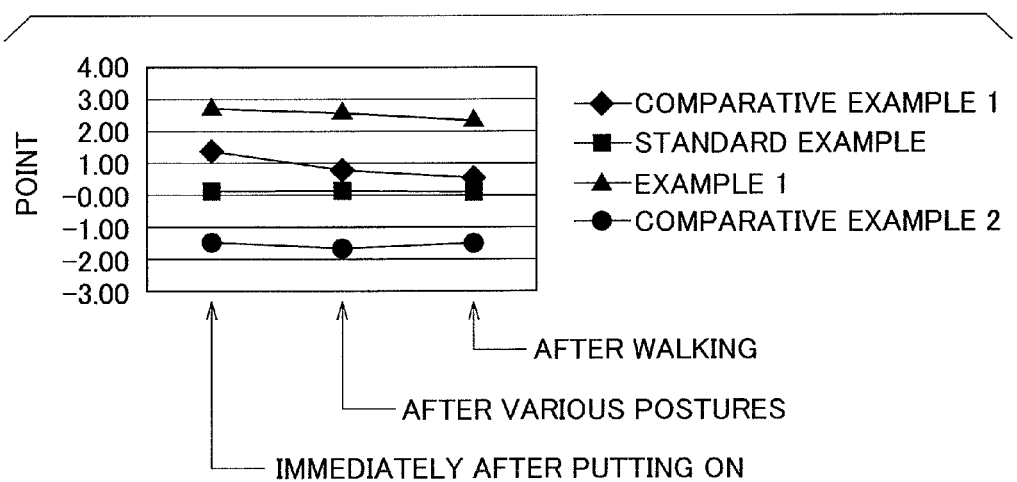
FIG. 8 is a chart showing the degree of comfort to the wearer's body of the main body of the disposable diaper.
Figure 9:
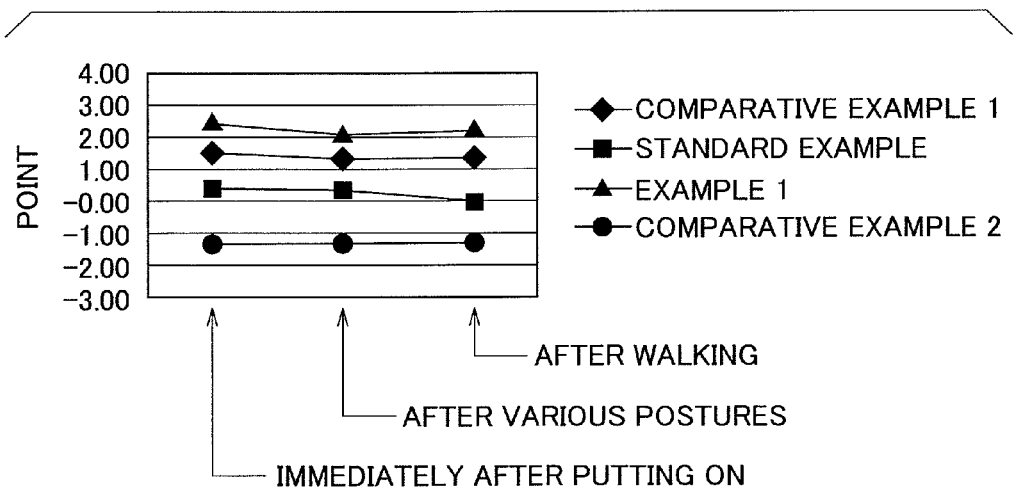
FIG. 9 is a chart showing the degree of softness to the touch of the absorbent body of the disposable diaper.

According to FIGS. 8 and 9, it was determined that Example 1 was of the best comfort to a wearer's body. It was also determined that the absorbent body 13 had the most pleasant texture. As a result of these assessments, Example 1 was found to be a disposable diaper of better comfort during wearing and of better adhesion than conventionally marketed disposable diapers.

What is claimed is:

1. A composite sheet comprising:
   a stretchable non-woven fabric which expands and contracts in at least one direction, the stretchable non-woven fabric comprising high-density regions and low-density regions arranged alternatively with each other in a stretching direction to allow expansion and contraction of the stretchable non-woven fabric;
   a non-stretchable non-woven fabric;
   a junction which binds intermittently the stretchable non-woven fabric to the non-stretchable non-woven fabric in the stretching direction;
   and a plurality of gathers which is formed by loosening a non-bound area of the non-stretchable non-woven fabric in a contracted state, and is arranged along a direction intersecting the stretching direction,
   wherein an apex of each gather does not reach the neighboring gather when the gathers lean to one side of the stretchable direction, and the high-density regions and the low-density regions are formed throughout the stretchable non-woven fabric including portions not including junctions.

2. The composite sheet of claim 1, wherein a weight basis of the stretchable non-woven fabric is greater than a weight basis of the non-stretchable non-woven fabric.

3. The composite sheet of claim 1, wherein the non-stretchable non-woven fabric has a basis weight of 10 to 50 $g/m^2$.

4. The composite sheet of claim 1, wherein the stretchable non-woven fabric has a basis weight of 10 to 80 $g/m^2$.

5. The composite sheet of claim 1, wherein the stretchable non-woven fabric has a strength in a 200% expanded state of 1 to 7 N/50 mm.

6. The composite sheet of claim 1, wherein the composite sheet has a weight basis of 30 to 200 $g/m^2$.

7. The composite sheet of claim 1, wherein the composite sheet has a weight basis of 65 to 105 $g/m^2$.

8. The composite sheet of claim 1, wherein the plurality of gathers are all tilted in one direction.

9. The composite sheet of claim 1, wherein the plurality of gathers are tilted alternating directions to face one another.

10. The composite sheet of claim 1, wherein the plurality of gathers are tilted randomly.

11. The composite sheet of claim 1, wherein the junction comprises a hot-melt adhesive.

12. The composite sheet of claim 11, wherein the hot melt adhesive comprises an elastomer-based resin.

13. The composite sheet of claim 11, wherein the weight basis of the hot melt adhesive is in the range of 1 to 5 $g/m^2$.

14. The composite sheet of claim 1, wherein the composite sheet satisfies the following formula in which A is a width in the stretching direction of the junction where the non-stretching non-woven fabric is bound to the stretching non-woven fabric, B is a length in the stretching direction of a region of the non-stretchable non-woven fabric not bound to the stretchable non-woven fabric, and C is a distance in the stretching direction between each of the junctions: B<C+2A.

15. The composite sheet of claim 1, wherein the composite sheet satisfies the following formula in which A is a width in the stretching direction of the junction where the non-stretching non-woven fabric is bound to the stretching non-woven fabric, B is a length in the stretching direction of a region of the non-stretchable non-woven fabric not bound to the stretchable non-woven fabric, and C is a distance in the stretching direction between each of the junctions: B<A+C.

* * * * *